United States Patent
Rutherford et al.

(10) Patent No.: US 9,957,764 B2
(45) Date of Patent: May 1, 2018

(54) CUTTING APPARATUS

(75) Inventors: Loren Rutherford, Dubai (AE); Olivier Jean-Marc Claude Mageren, Brussels (BE); Khac Nguyen Che, Brussels (BE)

(73) Assignee: Halliburton Energy Services, Inc., Houston, TX (US)

( * ) Notice: Subject to any disclaimer, the term of this patent is extended or adjusted under 35 U.S.C. 154(b) by 1091 days.

(21) Appl. No.: 13/979,275

(22) PCT Filed: Jan. 11, 2012

(86) PCT No.: PCT/EP2012/050394
§ 371 (c)(1),
(2), (4) Date: Oct. 23, 2013

(87) PCT Pub. No.: WO2012/095468
PCT Pub. Date: Jul. 19, 2012

(65) Prior Publication Data
US 2014/0033836 A1    Feb. 6, 2014

Related U.S. Application Data

(60) Provisional application No. 61/431,746, filed on Jan. 11, 2011.

(51) Int. Cl.
*B62D 1/18* (2006.01)
*B26D 3/00* (2006.01)
(Continued)

(52) U.S. Cl.
CPC ............ *E21B 25/005* (2013.01); *B23D 21/02* (2013.01); *B26D 3/001* (2013.01); *B26D 1/18* (2013.01);
(Continued)

(58) Field of Classification Search
CPC .. B26D 3/001; B26D 1/18; B26D 7/01; E21B 25/005; B23D 21/02; B23D 55/043;
(Continued)

(56) References Cited

U.S. PATENT DOCUMENTS 1,857,693 A    5/1932   Quintrell
3,709,095 A *  1/1973   Laumer .................... B23C 3/30
                                               409/132
(Continued)

FOREIGN PATENT DOCUMENTS

CA    2200291    *  9/1997
JP    H0842752   *  2/1996
JP    2006133169    5/2006  ............... G01N 1/08

OTHER PUBLICATIONS

Australian Office Action, Application No. 2012206560; 4 pages, dated Oct. 6, 2015.
(Continued)

*Primary Examiner* — Gedeon M Kidanu
(74) *Attorney, Agent, or Firm* — Baker Botts L.L.P.

(57) ABSTRACT

Described herein is a cutting apparatus (100) for allowing visual inspection of a core sample in an inner tube at a drilling site after the inner tube has been removed from a coring tube and prior to it being transported to a laboratory. The cutting apparatus (100) comprises a support track (110, 112, 114, 116)) on which is mounted a tube support member (120), a cutter wagon (130, 132, 138) and a drive arrangement (140, 142, 144, 146). The apparatus (100) provides relative movement between an inner tube (150) and the cutter wagon (130, 132, 138) to allow a section of the inner tube (150) to be removed along its entire length for visual inspection. The drive arrangement (140, 142, 144, 146) provides the relative movement between the inner tube (150) and the cutter wagon (130, 132, 138).

14 Claims, 4 Drawing Sheets

(51) Int. Cl.
  E21B 25/00 (2006.01)
  G01N 1/04 (2006.01)
  B23D 21/02 (2006.01)
  B26D 1/18 (2006.01)
  B26D 7/01 (2006.01)

(52) U.S. Cl.
  CPC ............... *B26D 7/01* (2013.01); *G01N 1/04* (2013.01); *Y10T 83/0267* (2015.04); *Y10T 83/0281* (2015.04); *Y10T 83/0289* (2015.04)

(58) Field of Classification Search
  CPC ...... B23D 59/006; B23D 59/04; B28D 1/086; B28D 7/04; G01N 1/04
  USPC .................................................. 83/870–887
  See application file for complete search history.

(56) References Cited

U.S. PATENT DOCUMENTS

| | | | | |
|---|---|---|---|---|
| 4,078,460 | A * | 3/1978 | Bowman | B27B 7/02 83/471.2 |
| 4,628,894 | A | 12/1986 | Stewart | |
| 4,674,473 | A * | 6/1987 | Stewart | B23D 55/043 125/1 |
| 5,398,579 | A * | 3/1995 | Bando | C03B 33/027 83/879 |
| 5,460,071 | A * | 10/1995 | Barrett | B09B 5/00 30/92.5 |
| 6,761,098 | B1 * | 7/2004 | Esping | B26D 3/001 83/102 |
| 7,107,891 | B2 * | 9/2006 | Kneppe | B23D 25/12 83/347 |
| 2003/0000358 | A1 | 1/2003 | Harris et al. | |
| 2008/0023202 | A1 | 1/2008 | Keatch et al. | |
| 2008/0083645 | A1 * | 4/2008 | Cravatte | E21B 25/00 206/730 |
| 2011/0167973 | A1 * | 7/2011 | Wadsworth | B26D 1/40 83/54 |

OTHER PUBLICATIONS

Australian Office Action; Application No. 2012206560; pp. 4, dated May 26, 2014.
International Search Report and Written Opinion, Application No. PCT/EP2012/050394, 10 pages, dated Mar. 14, 2013.
Canadian Office Action; Application No. 2,823,777; pp. 2, dated May 26, 2014.
International Preliminary Report on Patentability; PCT/EP2012/050394; pp. 8, dated Jul. 25, 2013.
Canadian Office Action; Application No. 2,823,777; pp. 4, dated Jun. 2, 2015.
Office Action, European Patent Application No. 12700182.4, 5 pages, dated Feb. 28, 2017.

* cited by examiner

CUTTING APPARATUS

RELATED APPLICATIONS

This application is a U.S. National Stage Application of International Application No. PCT/EP2012/050394 filed Jan. 11, 2012, which designates the United States and claims the benefit of U.S. Provisional Patent Application Ser. No. 61/431,746 filed Jan. 11, 2011, which are incorporated herein by reference in their entirety.

The present invention relates to cutting apparatus and is more particularly, although not exclusively, concerned with an inner tube splitter for splitting inner tubes used to obtain core samples.

In the oil and gas industries, it is well known to extract core samples for providing geological and geophysical data relating to a subterranean formation into which drilling is to be done extensively. Core samples are typically retrieved at a drilling site using coring equipment which includes an inner tube housed within a coring tube. The inner tube forms a receptacle for receiving the core sample, and, the inner tube is removed from the coring tube prior to being transported to a laboratory where tests are carried out on the sample within the inner tube.

However, it is often desired to be able to inspect visually the core sample at the drilling site prior to it being transported for detailed testing. In order to be able to achieve such a visual inspection, the inner tube must be cut. The cutting process may contaminate the sample as the inner tube is cut.

In US 2008/0083645, an inner tube that comprises two receptacle portions that together form a cylindrical tube having a circular cross-section is disclosed. The two receptacle portions of the inner tube are joined together using a pair of connecting inserts that extend along the entire length of the inner tube. Opening the inner tube to allow on-site visual inspection of the sample requires the use of a tool, such as a crow bar, that can be inserted between the two receptacle portions and moved so as to apply a force to separate the receptacle portions. The applied force urges the connecting inserts out of engagement with one of the receptacle portions. Both connecting inserts need to be released on either side of the inner tube so that one of the receptacle portions can be removed to reveal the sample for visual inspection.

Whilst the inner tube described in US 2008/0083645 permits accessibility to the core sample for visual inspection at a drilling site without axial withdrawal of the core sample from the inner tube, the use of a tool to separate the two receptacle portions of the inner tube can still cause damage to the core sample as each receptacle portion is damaged in the separation process.

It is therefore an object of the present invention to provide a method for enabling visual inspection of a core sample within an inner tube without damaging the core sample as the inner tube is opened.

It is a further object of the present invention to provide cutting apparatus that enables the inner tube to be opened without damaging the core sample.

In accordance with a first aspect of the present invention, there is provided cutting apparatus for cutting a tube longitudinally along its length, the apparatus comprising: a support track for supporting the tube in at least one cutting position; at least one cutter assembly mounted with respect to the track; and a drive arrangement for providing relative movement between each cutter assembly and the support track.

Each cutter assembly preferably comprises at least one cutter wheel which is adjustable to determine the depth of cut along the length of the tube.

Additionally, each cutter assembly may include at least one stabilising device that stabilises the tube in each cutting position. Such a stabilising device may comprise at least one roller element. Preferably, each roller element comprises a diabolo roller.

Moreover, each cutter assembly may further include a tube support for supporting the tube in each cutting position. Alternatively, the support track may include a tube support for supporting the tube in each cutting position.

Ideally, each cutter assembly comprises a frame mountable on the support track. In this case, each cutter wheel may be rotatable with respect to at least a portion of the frame about a longitudinal axis extending along and parallel to the support track.

In each cutter assembly, first and second cutter wheels may be provided, at least one of the first and second cutter wheels being rotatable with respect to the at least a portion of the frame to define an angle between the first and second cutter wheels. Additionally, the first and second cutter wheels may define an angle. Such an angle may substantially be in the range between 30° and 180°.

The drive arrangement may comprise a pulley arrangement mounted with respect to the support track. Alternatively, the drive arrangement may comprise a rack and pinion arrangement mounted on the support track.

In accordance with another aspect of the present invention, there is provided a method of visually inspecting a core sample extracted at a drilling site, the method comprising the steps of: providing a receptacle containing the core; using cutting apparatus to produce at least one cut along the length of the receptacle; removing a portion of the receptacle that has been produced by said at least one cut; and visually inspecting the core sample through an aperture formed by the removed portion of the receptacle.

The cutting step may comprise providing relative motion between the receptacle and the cutting apparatus.

Two cuts are preferably provided along the length of the receptacle to define the portion that is to be removed to produce the aperture. Preferably, the two cuts are produced substantially simultaneously.

In one embodiment, the portion of the receptacle that is removed comprises a segment of a circle. The segment of the circle preferably subtends an angle substantially in the range between 30° and 180°.

Advantageously, as the present invention relates to providing access to a core sample within an inner tube, the inner tube itself does not need to be modified in any way and therefore there is no impact on drilling equipment used to extract the core sample. It will be appreciated that the present invention can be used for any inner tube that can be inserted within a coring barrel. Moreover, as there are no modifications required to the inner tube, there is no risk of jamming of the inner tube within the core barrel.

For a better understanding of the present invention, reference will now be made, by way of example only, to the accompanying drawings in which.

Figure 1:
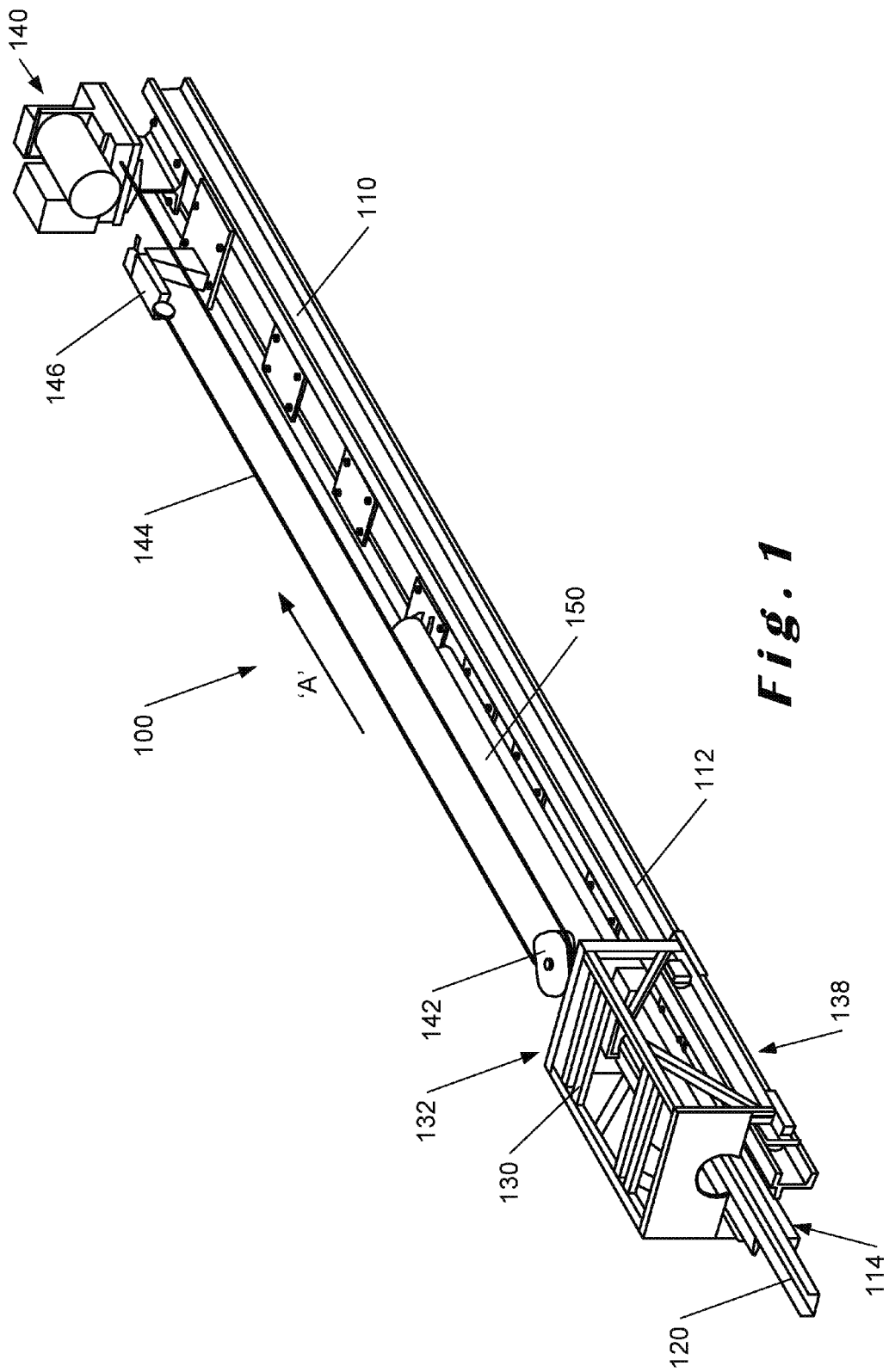
FIG. 1 illustrates a perspective view of cutting apparatus in accordance with the present invention.

FIGS. 3 to 6 respectively illustrate various configurations of cutter wheels that can be used in the cutting apparatus of FIG. 1.

The present invention will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes.

It will be understood that the terms "vertical" and "horizontal" are used herein refer to particular orientations of the Figures and these terms are not limitations to the specific embodiments described herein.

In the drawings, an empty inner tube is shown but it will readily be appreciated that, in operation at a drilling site, the inner tube will contain a core sample.

The present invention relates to a method and apparatus for cutting an inner tube of a core barrel to reveal at least a portion along the entire length of the tube for visual inspection. Cutter wheels are used to cut the inner tube but they are not motorised so that they protect the core sample within the inner tube against potential damage and contamination. The invention requires relative movement between the inner tube and the cutter wheels and it may be the cutter wheels that move relative to the inner tube along its length or the inner tube may move relative to cutter wheels that are in a fixed position. It will be appreciated that the choice for implementation of the relative movement will be determined by the particular application and other constraints, such as, space.

In accordance with the present invention, the inner tubes are cut longitudinally along their entire length so that a portion of the tube can readily be removed. This provides direct access to the core sample within the inner tube. In addition, as there is no motorisation of the cutter wheels, vibrations from the cutting operation are not transferred to the core sample thereby changing it properties. Damage to the core is also prevented when compared to a conventional rotating circular saw. The core sample is protected against shocks, contamination, cracks and intrusion using the present invention.

Additionally, lengths of up to 9 m (30 ft) can be cut to reveal the core sample for visual inspection along the entire length. The present invention is safe and easy to use and does not provide any loose cuttings that may be hazardous to the working environment or may contaminate the core sample.

The present invention can also be used to cut inner tubes made of different materials, for example, those made of aluminium, steel or fibreglass.

Referring initially to FIG. 1, cutting apparatus 100 in accordance with the present invention is shown. The apparatus 100 comprises a support track 110 on which is mounted a tube support member 120, a cutter wagon 130 and a drive arrangement 140. A tube 150 that is to be cut using the cutting apparatus 100 is also shown.

The support track 110 includes two track elements 112, 114 arranged on either side of a central portion 116 that supports the tube 150. The two track elements 112, 114 are used to guide the cutter wagon 130 along the length of the support track 110 as it cuts the tube 150. Track element 114 is shown more clearly in FIG. 2. The cutter wagon 130 will be described in more detail below with reference to FIG. 2.

As shown in FIG. 1, the tube support member 120 forms part of the cutter wagon 130 and moves with it along the central portion 116 of the support track 110 under control of the drive arrangement as the tube 150 is cut. Alternatively, the cutter wagon 130 and tube support member 120 may be stationary and the tube 150 is moved relative thereto to provide the cutting operation.

In the embodiment shown in FIG. 1, the drive arrangement 140 includes a pulley 142 mounted on the cutter wagon 130 and a drive wire 144 that is fixed to a stop 146 and to a winding mechanism (not shown) within the drive arrangement 140. As shown, the drive wire 144 passes from stop 146, through the pulley 142 and into the drive arrangement 140. Activation of the winding mechanism within the drive arrangement 140 shortens the drive wire 144 to pull the cutter wagon 130 towards the drive arrangement 140 in the direction of arrow 'A'.

Figure 2:
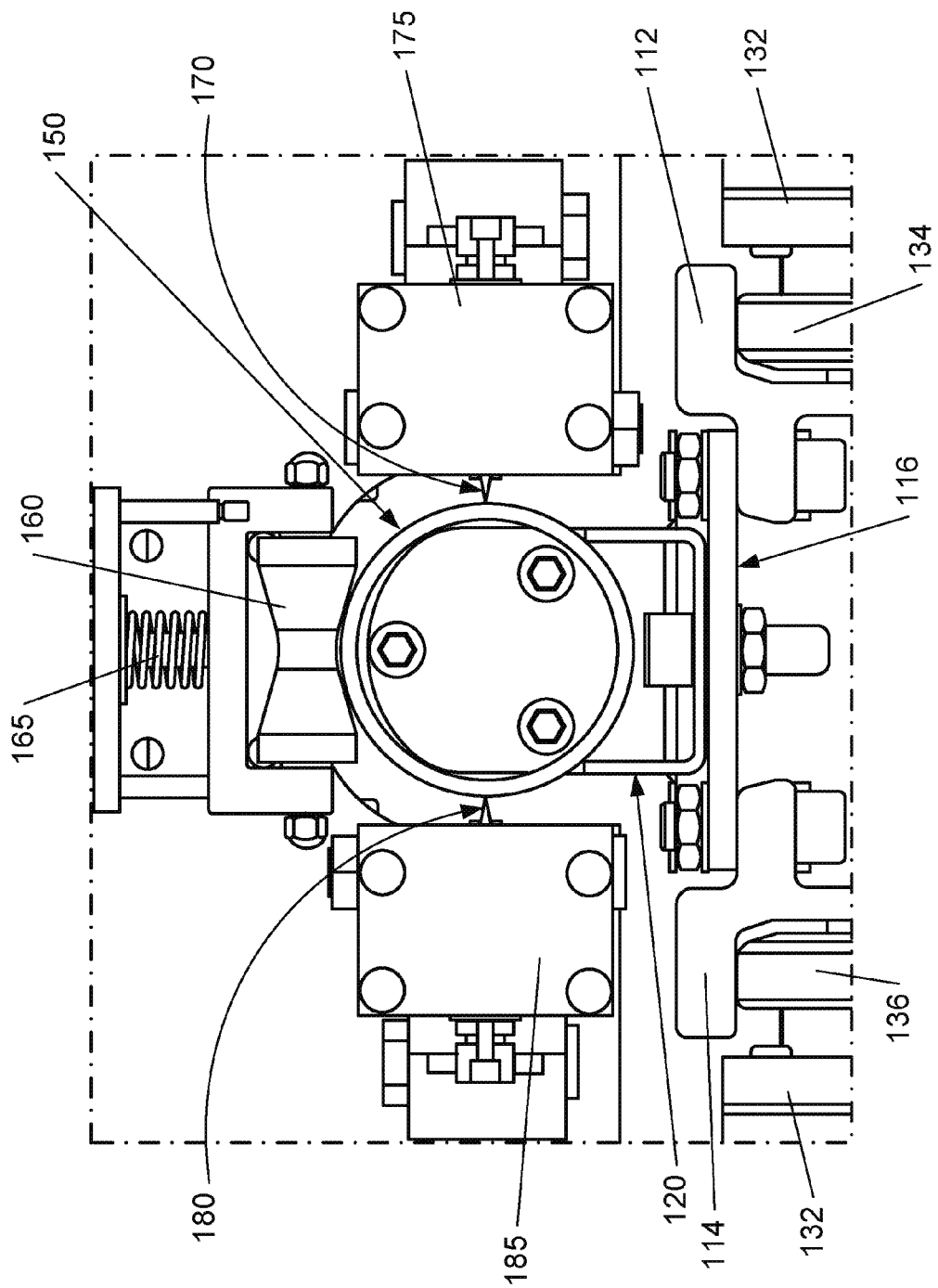
FIG. 2 illustrates an end view of the cutting apparatus of FIG. 1.

The cutter wagon 130 comprises a frame 132 which includes guide runners 134, 136 that engage respective ones of the track elements 112, 114 as shown more clearly in FIG. 2. In this case, two of guide runners are provided on each side of the frame 132 and each guide runner is connected to or associated with a transverse portion 138 of the frame 132 (shown in FIG. 1). The transverse portion 138 of the frame 132 is substantially parallel to respective ones of the track elements 112, 114. It will be appreciated that any number of guide runners can be provided on the transverse portion 133 of the frame 132 for engaging the track elements 112, 114.

Although not shown in FIG. 1, the tube support 120 extends the entire length of the support track 110 and is mounted on the central portion 116 thereof (FIG. 2). It will, however, be appreciated that the tube support 120 may only be required to provide support for the tube 150 in a cutting position and may be associated with the cutter wagon 130 and not the support track 110.

Turning now to FIG. 2, an end view of the cutting apparatus 100 is shown. Components that have previously been described with reference to FIG. 1 are referenced the same. In FIG. 2, the frame 132 of the cutter wagon 130 is not shown for clarity.

Inside the cutter wagon 130 and fixed to an upper portion of the frame 132 thereof is a diabolo roller 160. The roller 160 is retained in position against the tube 150 to be cut by a spring arrangement 165 so that the tube 150 is aligned in a correct cutting position. The diabolo roller 160 also ensures that the tube 150 does not move within the tube support 120 as it is being cut.

Although a single diabolo roller 160 is shown in FIG. 2, it will be appreciated that more than one such roller can be employed to ensure that the tube 150 is retained in place during the cutting operation. For example, one diabolo roller may be located at each end of the frame 132 of the cutter wagon 130 and spaced in a direction aligned with the length of the support track 110. It will also be appreciated that the orientation of each diabolo roller 160 with respect to the tube 150 does not need to be such that it provides only a downward force due to the action of the spring arrangement 165. Other diabolo rollers may be used to provide locating forces in other planes.

Moreover, although diabolo rollers are described which effectively provide two contact surfaces with the tube that is being guided and/or supported during the cutting operation, other means of holding the tube in the correct position against the tube support 120 for cutting may be employed.

In the specific embodiment shown in FIG. 2, two cutting wheels 170, 180 are shown. Each cutting wheel 170, 180 is mounted within a support block 175, 185 which can be adjusted to ensure that its associated cutting wheel 170, 180 is in the correct position to provide the required depth of cut, that is, it cuts only the tube 150 and does not extend into the core sample (not shown). In this embodiment, the cutting wheels 170, 180 are arranged to cut the tube to produce two identical portions, each subtending an angle of 180°, that allow one portion to be separated from the other portion thereby allowing a visual inspection of the core sample contained therein.

It will, however, be appreciated that the cutting apparatus in accordance with the present invention can be used to provide other cuts that provide portions that subtend angles other than 180°. For example, one cutter wheel could be aligned at any suitable angle between 30° and 180° with respect to the other cutter wheel to provide a suitable window through which the core sample can be inspected on the drilling site.

Moreover, although a pulley arrangement has been described above for effecting the relative movement between the tube and the cutter wheel or wheels, it will be appreciated that other suitable arrangements can be used to provide the required relative movement. For example, a rack and pinion arrangement mounted on the support track could also be used.

Although the cutter apparatus described with respect to FIGS. 1 and 2 has two cutter wheels, it will be understood that a single cutter wheel can be used with a suitable arrangement for providing relative rotation of the cutter wheel between a first and a second cutting position. In FIGS. 3 to 6, various cutter wheel assemblies are shown.

Figure 3:
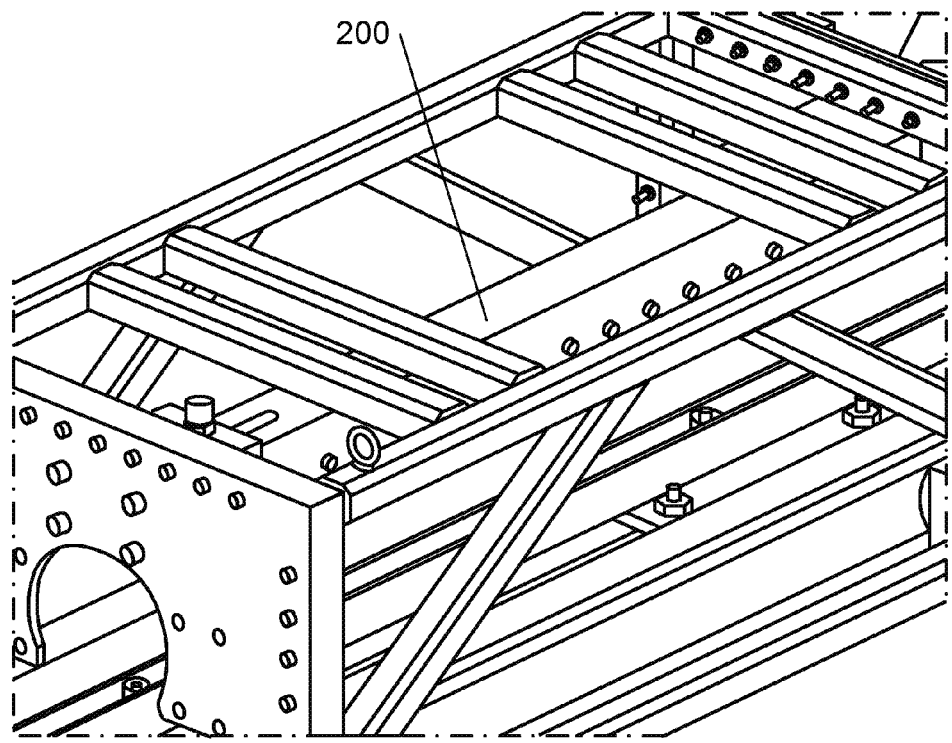
Figure 4:
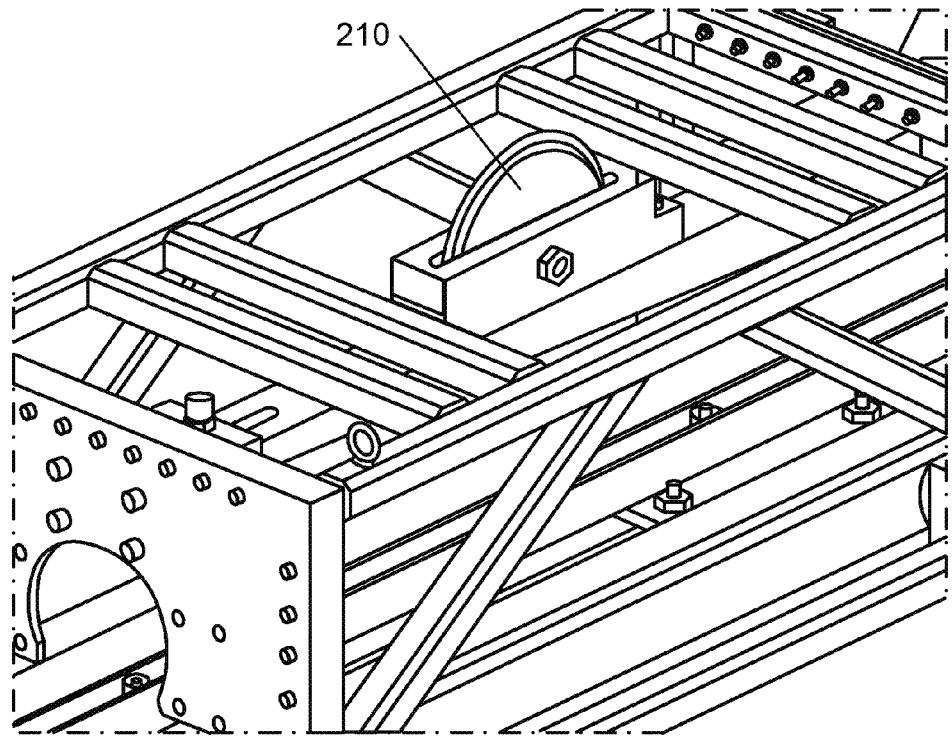
Figure 5:
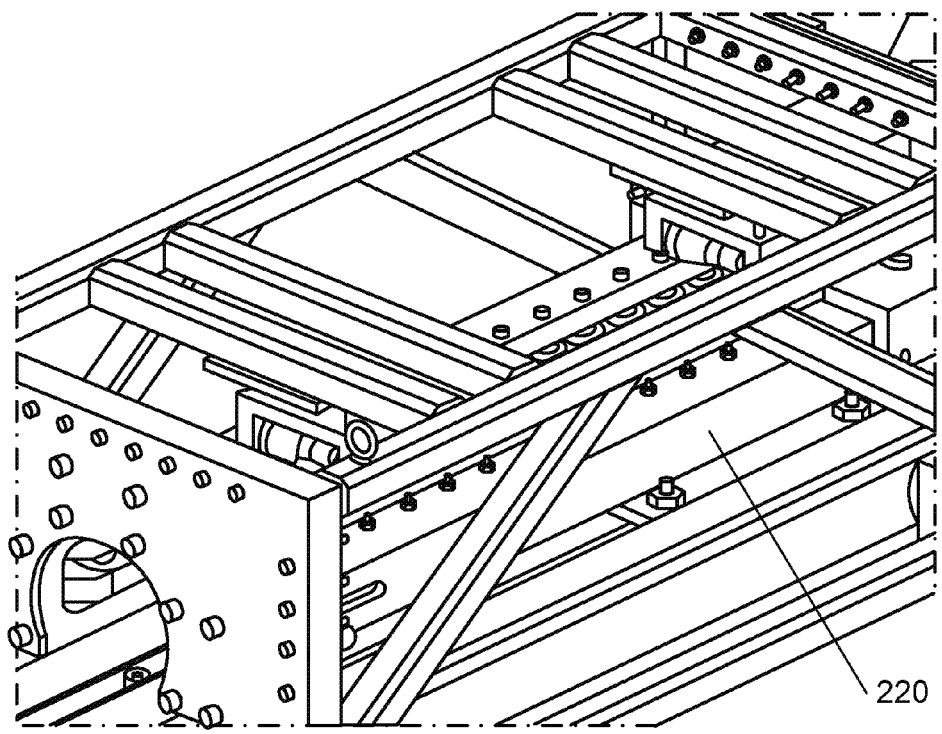
Figure 6:
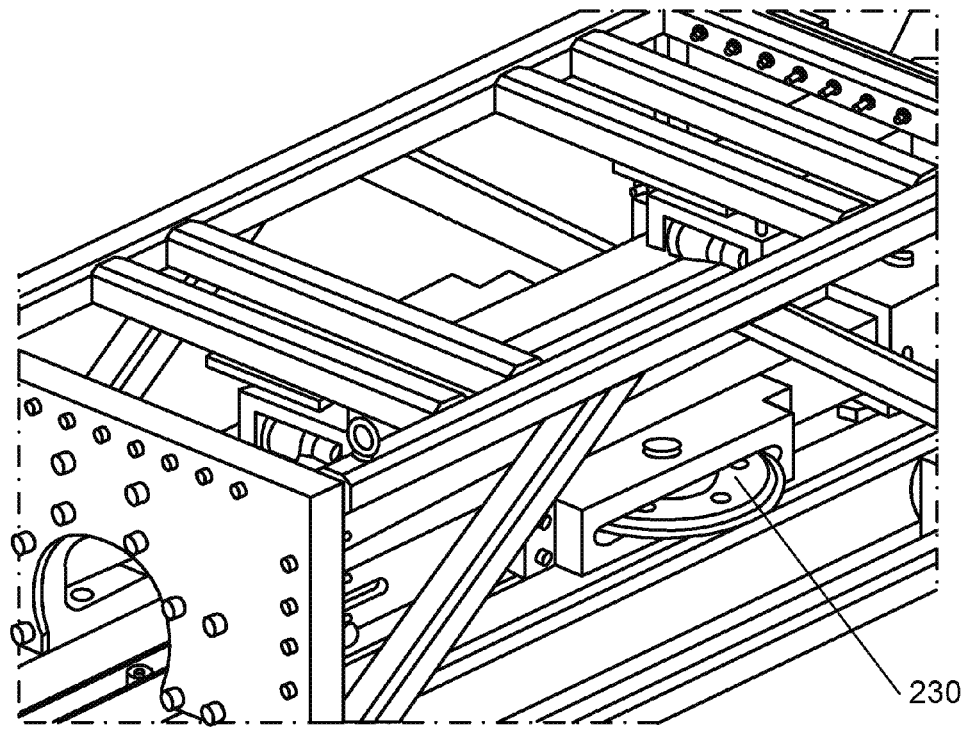

In FIG. 3, a small cutter wheel assembly 200 is shown in which the cutter wheel assembly is mounted vertically with respect to the frame 132. Similarly, FIG. 4 shows a large cutter wheel assembly 210 that is also mounted vertically with respect to the frame 132. In FIGS. 5 and 6, respective small and large cutter wheel assemblies 220, 230 are shown that are mounted horizontally or laterally with respect to the frame 132. The cutter wheel assemblies 220, 230 can be used in the specific embodiment of the cutting apparatus described above with reference to FIGS. 1 and 2.

It will readily be appreciated that, although the present invention has been described with reference to a cutting wheel being used for cutting the tube, other cutting apparatus can be used, for example, a diamond stylus or other non-rotating cutting tool.

Although the present invention has been described with reference to specific embodiments, it will readily be appreciated that other embodiments of the cutting apparatus can be implemented without departing from the spirit and scope of the present invention.

The invention claimed is:

1. Cutting apparatus for cutting a tube longitudinally along its length, the apparatus comprising:
   a support track for supporting the tube in at least one cutting position;
   at least one cutter assembly mounted with respect to the track, the at least one cutter assembly including at least one cutting tool that is spring arranged; and
   a drive arrangement for providing relative movement of the at least one cutter assembly along the support track.

2. Cutting apparatus according to claim 1, wherein the at least one cutting tool is a cutter wheel which is adjustable to determine the depth of cut along the length of the tube.

3. Cutting apparatus according to claim 1, wherein the support track comprises a tube support for supporting the tube in the at least one cutting position.

4. Cutting apparatus according to claim 1, wherein the drive arrangement comprises a pulley arrangement mounted with respect to the support track.

5. Cutting apparatus according to claim 1, wherein the drive arrangement comprises a rack and pinion arrangement mounted on the support track.

6. Cutting apparatus according to claim 1, wherein the at least one cutter assembly comprises at least one stabilising device that stabilises the tube in the at least one cutting position.

7. Cutting apparatus according to claim 6, wherein the at least one cutter assembly further comprises a tube support for supporting the tube in the at least one cutting position.

8. Cutting apparatus according to claim 6, wherein the at least one stabilising device comprises at least one roller element.

9. Cutting apparatus according to claim 8, wherein the at least one roller element comprises a diabolo roller.

10. Cutting apparatus according to claim 1, wherein the at least one cutter assembly comprises a frame mountable on the support track.

11. Cutting apparatus according to claim 10, wherein the at least one cutting tool is a cutter wheel is rotatable with respect to at least a portion of the frame about a longitudinal axis extending along and parallel to the support track.

12. Cutting apparatus according to claim 10, the at least one cutting tool comprises first and second cutter wheels, the first and second cutter wheels defining an angle between the first and second cutter wheels.

13. Cutting apparatus according to claim 10, wherein the at least one cutting tool comprises first and second cutter wheels, at least one of the first and second cutter wheels being rotatable with respect to the at least a portion of the frame to define an angle between the first and second cutter wheels.

14. Cutting apparatus according to claim 13, wherein the angle between the first and second cutter wheels is substantially in a range between 30° and 180°.

\* \* \* \* \*